(12) United States Patent
Chudik

(10) Patent No.: US 11,406,505 B2
(45) Date of Patent: Aug. 9, 2022

(54) GLENOID IMPLANT WITH REPLACEABLE ARTICULATING PORTION

(71) Applicant: Steven C. Chudik, Western Springs, IL (US)

(72) Inventor: Steven C. Chudik, Western Springs, IL (US)

( * ) Notice: Subject to any disclaimer, the term of this patent is extended or adjusted under 35 U.S.C. 154(b) by 17 days.

(21) Appl. No.: 16/602,164

(22) Filed: Aug. 20, 2019

(65) Prior Publication Data
US 2021/0052393 A1 Feb. 25, 2021

(51) Int. Cl.
*A61F 2/40* (2006.01)
*A61F 2/30* (2006.01)

(52) U.S. Cl.
CPC ........ *A61F 2/4081* (2013.01); *A61F 2/30734* (2013.01); *A61F 2/40* (2013.01); *A61F 2002/3093* (2013.01); *A61F 2002/30261* (2013.01); *A61F 2002/30324* (2013.01); *A61F 2002/30331* (2013.01); *A61F 2002/30405* (2013.01); *A61F 2002/30604* (2013.01); *A61F 2002/4085* (2013.01)

(58) Field of Classification Search
CPC ...... A61F 2/4081; A61F 2/40; A61F 2/30734; A61F 2002/4085; A61F 2002/30604; A61F 2002/30405; A61F 2002/30331; A61F 2002/30261; A61F 2002/30324; A61F 2002/3093
See application file for complete search history.

(56) References Cited

U.S. PATENT DOCUMENTS

| | | | |
|---|---|---|---|
| 9,974,658 B2 | 5/2018 | Chudik | |
| 2011/0153023 A1* | 6/2011 | Deffenbaugh | A61F 2/4081 623/19.11 |
| 2013/0150972 A1* | 6/2013 | Iannotti | A61F 2/30734 623/18.11 |

* cited by examiner

*Primary Examiner* — Dinah Baria
(74) *Attorney, Agent, or Firm* — Erickson Law Group, PC

(57) ABSTRACT

The glenoid implant described here addresses wear of the implant's portion which articulates with a humeral head, and also addresses a frequent need to reverse the normal glenoid and humeral articulating surfaces. The new glenoid implant provides a coupling portion between the implant's bone fixation portion, which joins the implant to the glenoid bone, and the implant's articulating portion which articulates on an opposing humeral head. The coupling portion is joined to the bone fixation portion firmly but is disengageable without requiring the bone fixation portion's replacement so that the articulating portion can be removed from the implant and replaced without changing either the coupling portion or the bone fixation portion.

24 Claims, 22 Drawing Sheets

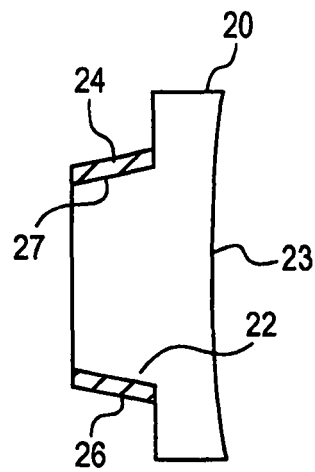
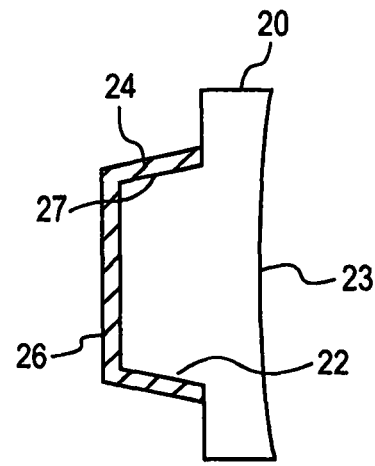
FIG. 5A            FIG. 5B
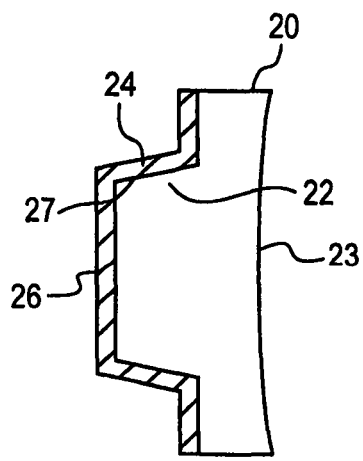
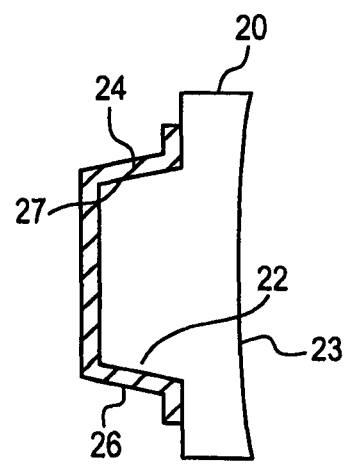
FIG. 5C            FIG. 5D

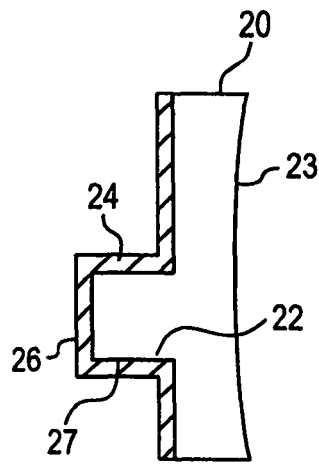 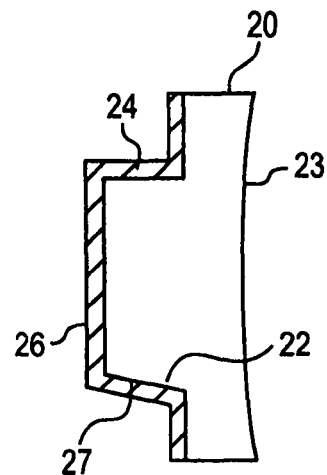 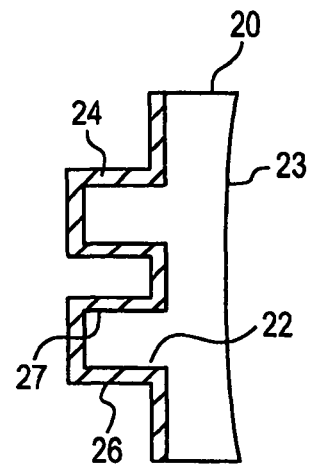
FIG. 5E    FIG. 5F    FIG. 5G
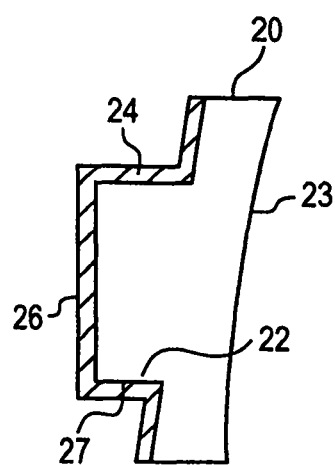 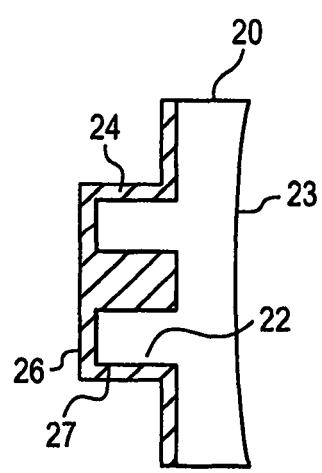 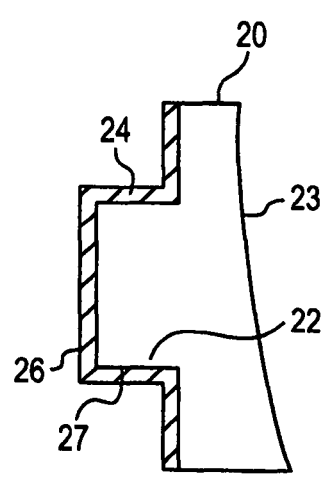
FIG. 5H    FIG. 5I    FIG. 5J

GLENOID IMPLANT WITH REPLACEABLE ARTICULATING PORTION

This nonprovisional application relates to systems for repairing and reconstructing injured shoulder joints. More particularly, it relates to improving the outcome of joint replacement surgery by providing a glenoid implant having an articulating portion which can be replaced, if it becomes worn, or converted to a reverse total shoulder arthroplasty, if that should be necessary, without disturbing the implant's connection to the glenoid bone. There are no other patent applications related to this one, and it is not subject to any federally sponsored research or development or to any joint research agreement.

BACKGROUND OF THE INVENTION

Orthopaedic surgeons often perform joint replacement surgery on patients who suffer pain and physical limitations caused by joint surfaces which have degenerative, traumatic, or other pathologic damage. The success of these surgeries is directly related to the degree of morbidity associated with the surgical technique which is used, and also to the ability of the surgery to restore the natural anatomy and biomechanics of the joint. Improving surgical success in both of these respects is the goal of the invention which is disclosed here.

BRIEF SUMMARY OF THE INVENTION

The new glenoid implant provides a stable, long lasting manner of engaging an implant in a patient's shoulder utilizing an improved junction between its articulating portion and the implant's bone fixation portion. This junction addresses the issue of implant wear to the articulating portion, making it possible to replace that portion without disturbing the implant's connection to the glenoid bone, and also addresses performing an easy conversion of the implant to a reverse total shoulder arthroplasty whenever that procedure is needed, as in the case of rotator cuff failure, for example.

Accordingly, one object of the present invention is to provide a novel glenoid implant for shoulder replacement surgery that can be implanted with conventional or minimally invasive techniques.

Another object of the present invention is to provide a glenoid implant which includes a bone fixation portion and an articulating wear-resistant portion along with an intermediate coupling portion which supplies a durable but detachable coupling between the bone fixation and articulating portions.

Another object of the present invention is to provide a glenoid implant which includes a bone fixation portion having geometry which affords long-lasting fixation of that portion to a glenoid bone and a durable and separable connection to a coupling portion of the implant engaged on an articulating wear-resistant portion of the implant.

Another object of the present invention is to provide a glenoid implant having a bone fixation portion which resides on the glenoid surface (onlay) and also in the glenoid vault (inlay) of a scapular bone.

Another object of the present invention is to provide a glenoid implant whole inlay and onlay design which allows the compressive forces of the glenohumeral joint to be transmitted to all aspects of the bone of the glenoid process and thereby encourage proper bone self-regulation and maintenance in response to these forces.

Another object of the present invention is to provide a glenoid implant which includes a bone fixation portion engaged to a scapular bone with screws.

Another object of the present invention is to provide a glenoid implant which includes an articulating portion arranged to reside within a glenoid vault.

Another object of the present invention is to provide a glenoid implant for correcting pathological conditions regarding offset, version, inclination, bone loss, bone fractures, medialization, joint instability and rotator cuff deficiency.

Another object of the present invention is to provide a glenoid implant with an articulating portion coupled to a firmly fixed bone fixation portion and exchangeable with another articulating portion without disturbing any previous fixation of the bone fixation portion.

Another object of the present invention is to provide a glenoid implant with an articulating portion which can be converted to a different articulating portion of alternative dimensions, material, and purpose while the bone fixation portion of the implant remains well fixed.

Another object of the present invention is to provide a glenoid implant having an articulating portion disposed in an anatomic total shoulder arthroplasty arranged for conversion to a reverse total shoulder arthroplasty and vice versa.

Other objects and advantages of this invention will be apparent to orthopaedic surgeons and other persons who are skilled in the art of shoulder repair and reconstruction, particularly after reviewing the following description of the preferred embodiments of the present invention and the accompanying drawings.

BRIEF DESCRIPTION OF THE DRAWINGS

FIG. 5A is an enlarged cross-sectional view of the new implant's coupling portion engaged with some of the sides of a non-articulating protruding element of the new implant's articulating portion.

FIG. 5B is an enlarged cross-sectional view of the new implant's coupling portion engaged upon the non-articulating protruding element of the new implant's articulating portion.

FIG. 5C is an enlarged cross-sectional view of the new implant's coupling portion engaged with the non-articulating side of the new implant's articulating portion.

FIG. 5D is an enlarged cross-sectional view of the new implant's coupling portion engaged with the non-articulating protruding element and other segments of the non-articulating side of the new implant's articulating portion.

FIG. 5E is an enlarged cross-sectional view of the new implant's coupling portion engaged with an offset protruding element of the new implant's articulating portion.

FIG. 5F is an enlarged cross-sectional view of the new implant's coupling portion engaged with an asymmetric protruding element of the new implant's articulating portion.

FIG. 5G is an enlarged cross-sectional view of the new implant's coupling portion engaged with a plurality of protruding elements of the new implant's articulating portion.

FIG. 5H is an enlarged cross-sectional view of the new implant's coupling portion engaged with an irregularly shaped non-articulating protruding element of the new implant's articulating portion.

FIG. 5I is an enlarged cross-sectional view of the new implant's coupling portion engaged with and over a plurality of non-articulating elements of the new implant's articulating portion.

FIG. 5J is an enlarged cross-sectional view of the new implant's coupling portion disposed opposite to an irregularly shaped articulating portion of the new implant.

DETAILED DESCRIPTION OF THE INVENTION

Figure 1:
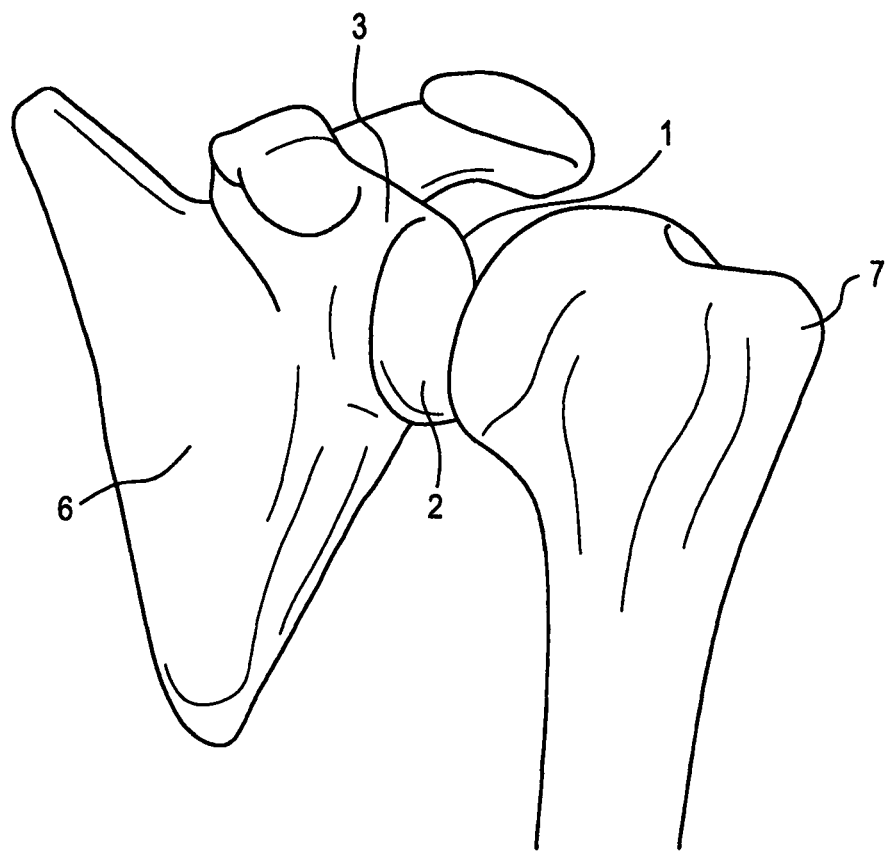
FIG. 1 is a perspective view of the principal members of a human glenohumeral anatomy, namely, the glenoid process of a scapula bone and the head of a humerus bone.
Figure 2A:
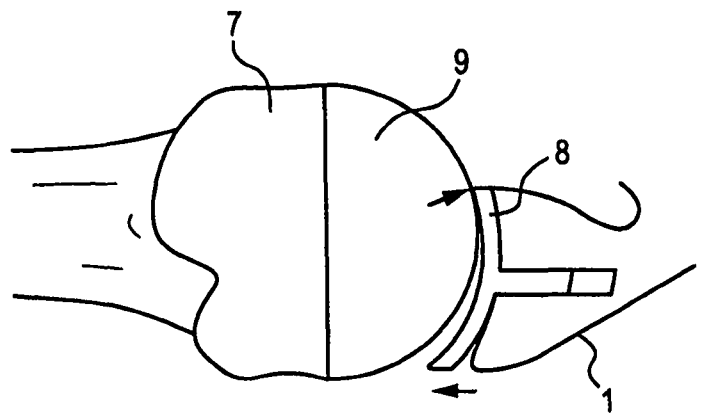
FIGS. 2A through 2C are perspective views, partially in section, of a humeral head engaging a traditional glenoid implant and illustrating the loosening complications in that engagement.
Figure 2B:
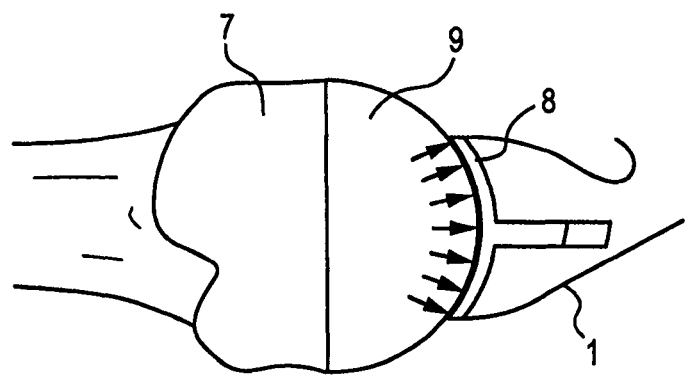
Figure 2C:
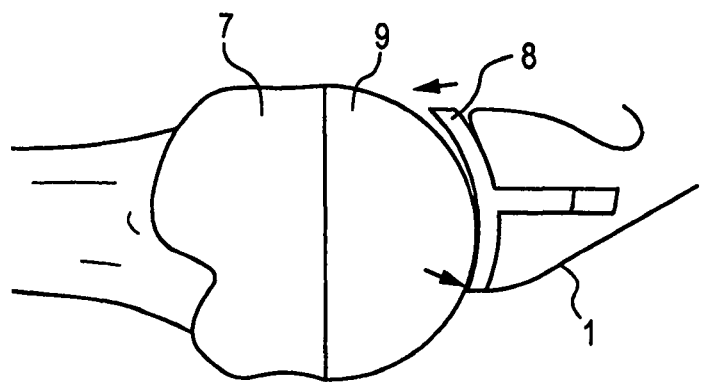

The new glenoid implant which is disclosed here is directed to the repair of a human shoulder, the principal skeletal members of which are illustrated in FIG. 1. Seen there, the glenoid process 1 of a scapula bone 6 includes a glenoid articular surface 2 located over the glenoid vault bone 3. The upper end of a humerus bone 7 is situated opposite the surface 2. The standard treatment for repairing this joint, illustrated in FIGS. 2A-2C, often involves installing a standard glenoid implant 8 in the glenoid process 1 for another implant 9 on the head of the humerus to articulate against. However, as further illustrated by the several positions of the implants 8 and 9 in FIGS. 2A-2C, the glenoid implant 8 is pressured in one direction and then another as the humeral implant 9 articulates against it. Frequently the result is that the glenoid implant 8 becomes worn, or loosens, and requires replacement. Sometimes, too, repair of the joint requires a reversal of the cooperating articulating surfaces so that the glenoid implant's articulating face must be convex, rather than concave, and the humeral implant's articulating face must be the reverse, concave instead of convex.

The new glenoid implant 30 solves these problems. Implant 30, illustrated in FIGS. 3 and 4, has three portions, namely, a bone fixation portion 10, an articulating portion 20, and a coupling portion 24 located intermediate the portions 10 and 20. The coupling portion, which engages both portions 10 and 20, forms a durable but disconnectable junction between the other two. The bone fixation portion 10 includes a hollow protruding element 11 with a bone ingrowth outer surface 15 for contacting and firmly joining a prepared surface of the glenoid inside the glenoid cavity. Also, on the inside wall of the protruding element 11, connecting surface 16 is arranged to engage the coupling portion 24 on a connecting surface 26 located on the outside of coupling portion 24's protruding element 24A. Similarly, on the inside wall of protruding element 24A of the coupling portion 24, connecting surface 27 is arranged to engage the articulating portion 20 on a connecting surface 22 located on the outside of the articulating portion 20's protruding element 20A.

The articulating portion 20 of the novel glenoid implant 30 includes either a relatively planar to slightly concave articulating surface element 23 for installation of the implant in an anatomic total shoulder arthroplasty or a convex articulating surface element 23A for installation of the implant in a reverse total shoulder arthroplasty.

The wall of the protruding element 11 of the bone fixation portion 10 can possess a variable wall thickness such that the opposite surfaces, the bone ingrowth surface 15 and the connecting surface 16, may possess different dimensions and shapes.

Figure 4:
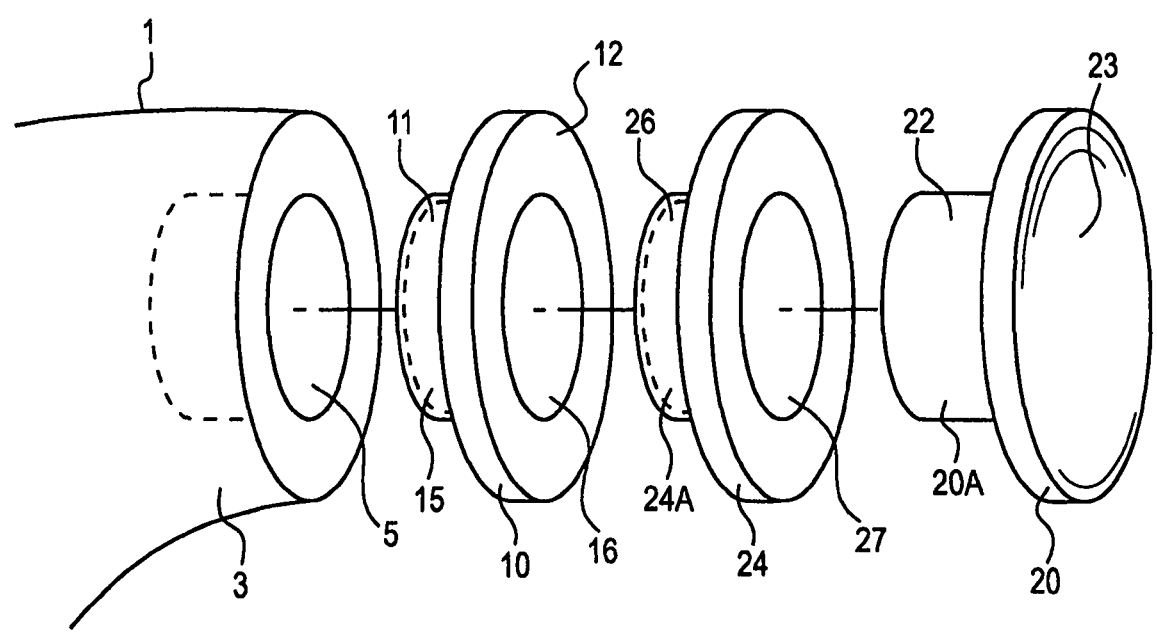
FIG. 4 is an exploded view of the new implant shown in FIG. 3 arranged for assembly with the glenoid.
Figure 6:
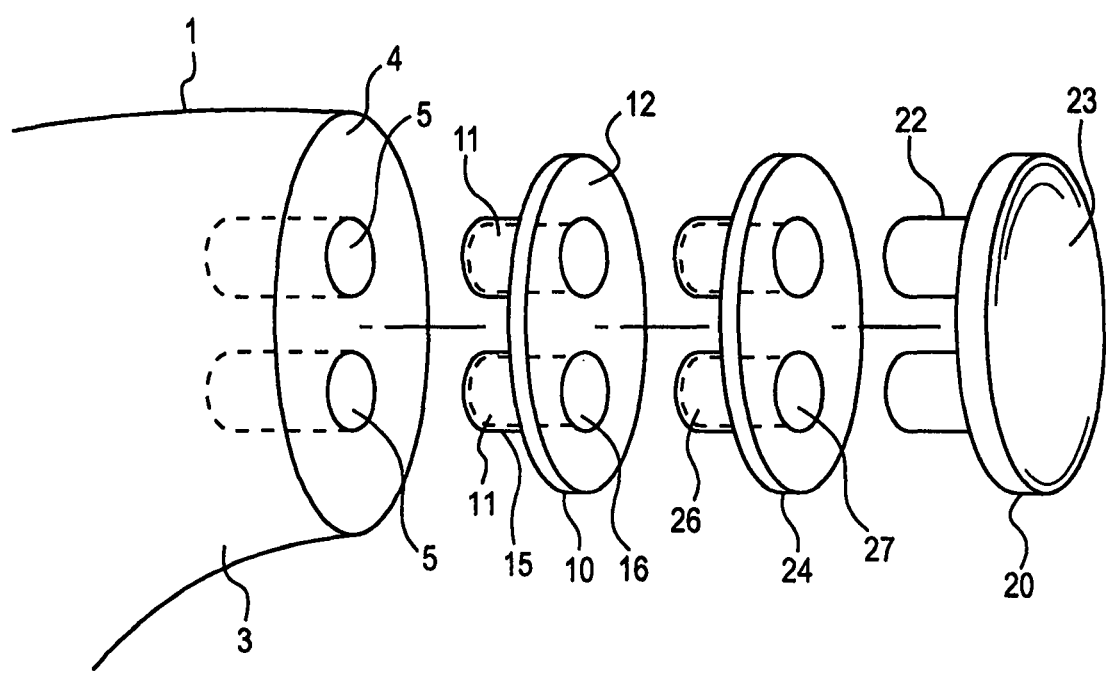
FIG. 6 is an exploded view of a configuration of the new implant which has multiple protruding elements instead of a single protruding element arranged for assembly with the glenoid.
Figure 7:
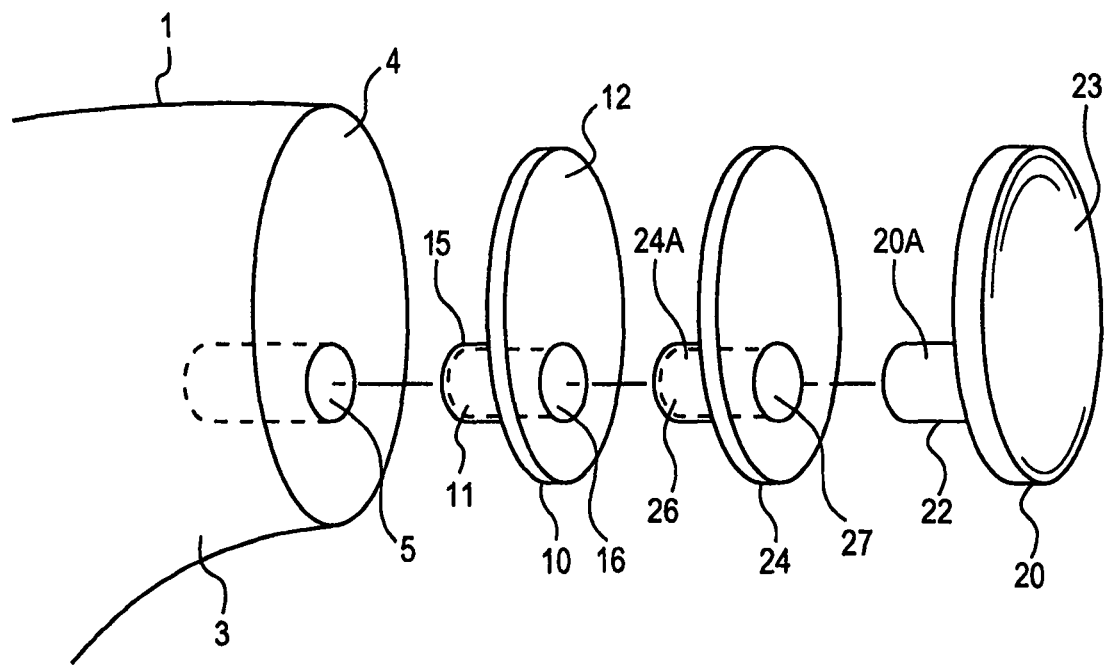
FIG. 7 is an exploded view of an offset configuration of a protruding element of the new implant arranged for assembly with the glenoid.

There may be a single protruding element 11 or multiple protruding elements 11 (FIGS. 4, 6). The protruding element 11 may also be offset (FIG. 7). The connecting surface 16 of the bone fixation portion 10 may be configured as a "bore" and the connecting surface 26 of the coupling portion 24 may also be configured as a "trunnion," composed of proper material with proper taper angle, diameter, length, conicity, surface finish, area of interference, and relative angle to allow a stable, long-lasting but disengageable connection between the bone fixation portion 10 and the articulating portion 20 by means of the intermediate coupling portion 24. The connecting surfaces 16 and 26 may possess more than one trunnion and bore, mating geometry other than conical, or an additional asymmetric engaging geometric configuration to restrict rotational movement of the articular portion 20.

Figure 3:
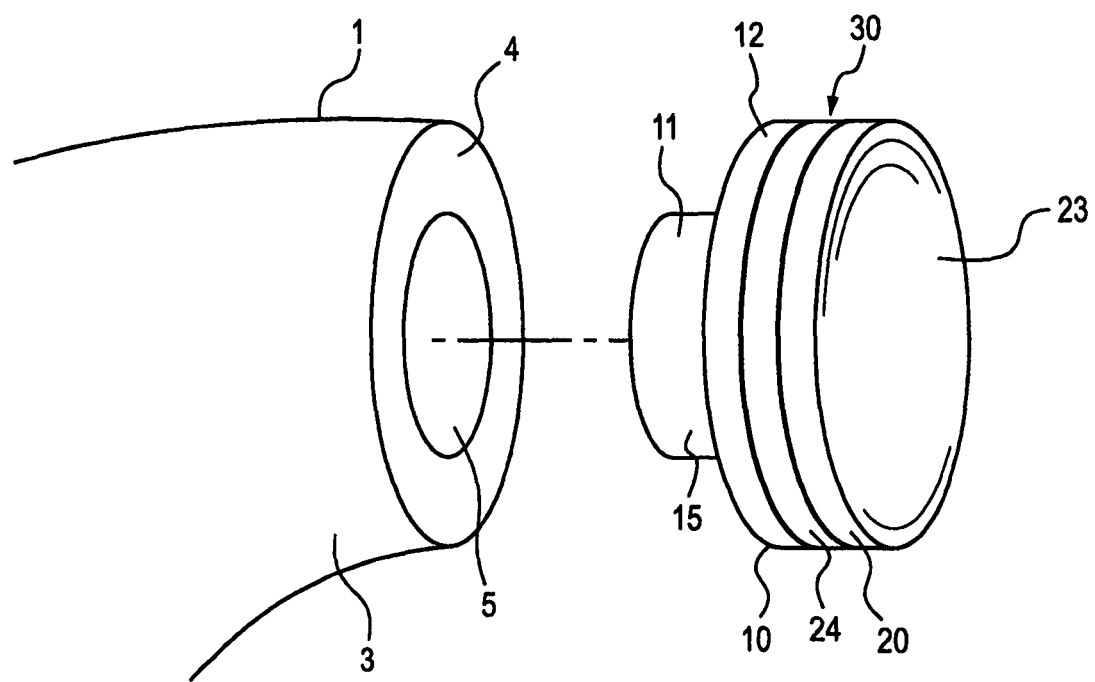
FIG. 3 is a perspective view of the new glenoid implant which is disclosed here having a wear-resistant articulating portion, an intermediate coupling portion and an implant bone-fixation portion designed to reside within a glenoid vault.
Figure 4A:
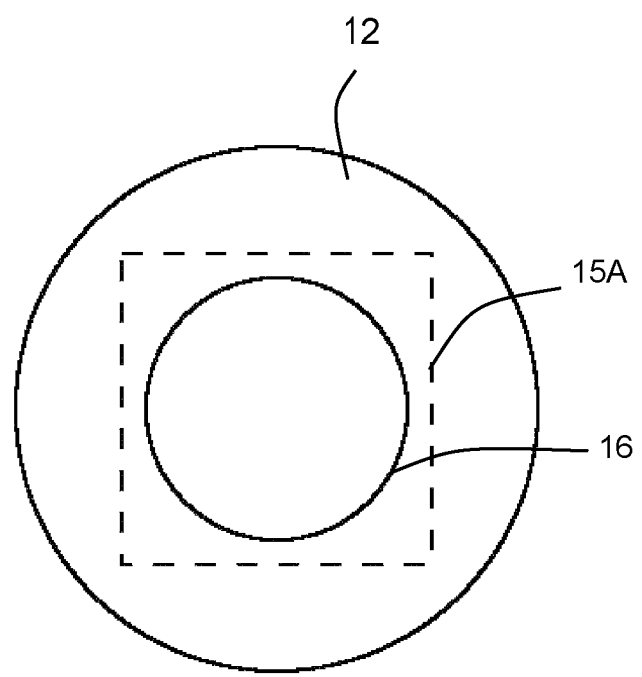
FIG. 4A is an end view of an embodiment of a bone-fixation portion of an embodiment of the new implant.
Figure 8:
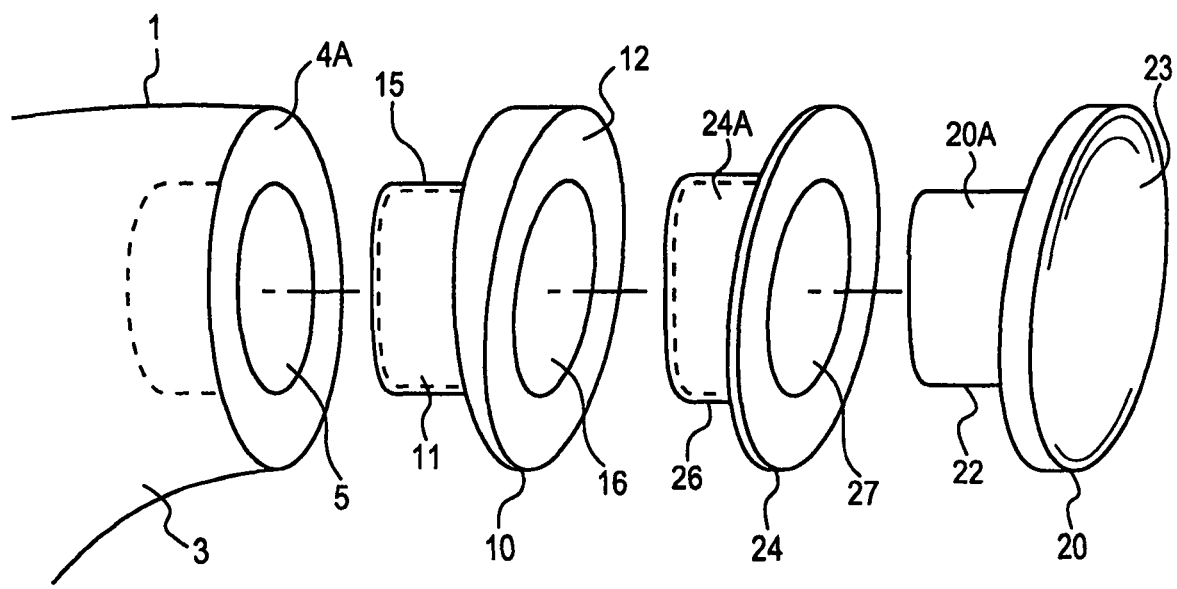
FIG. 8 is an exploded view of an alternative configuration of the new implant's bone fixation portion to correct for abnormalities in glenoid version and tilt, arranged with the intermediate coupling portion and articulating portion for assembly with the glenoid.
Figure 9:
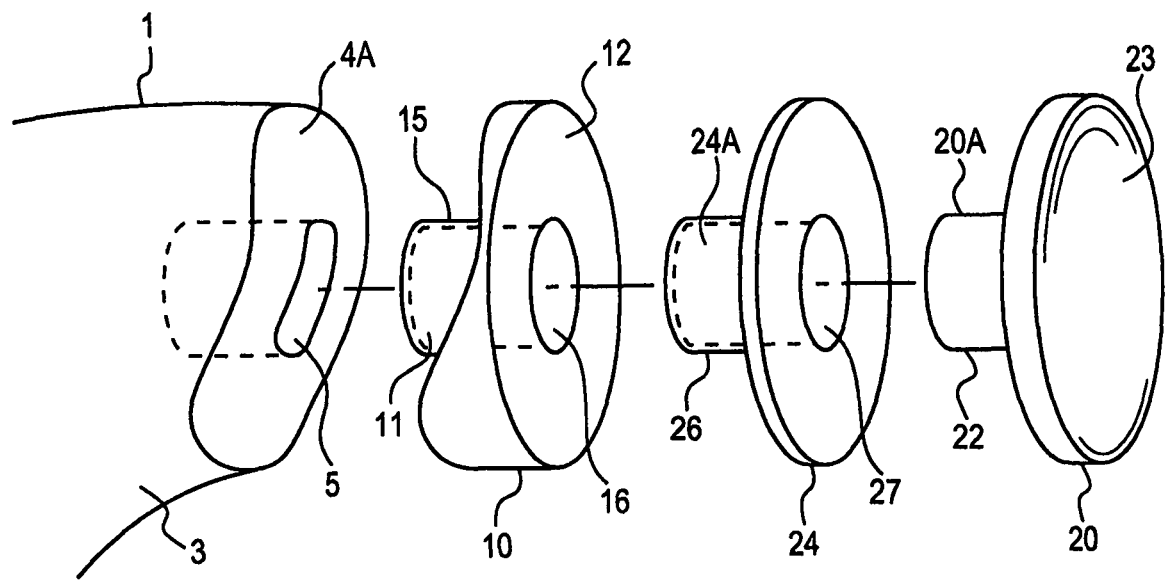
FIG. 9 is an exploded view of another alternative configuration of the new implant's bone fixation portion to accommodate glenoid deformity, arranged with the intermediate coupling portion and articulating portion for assembly with the glenoid.
Figure 10:
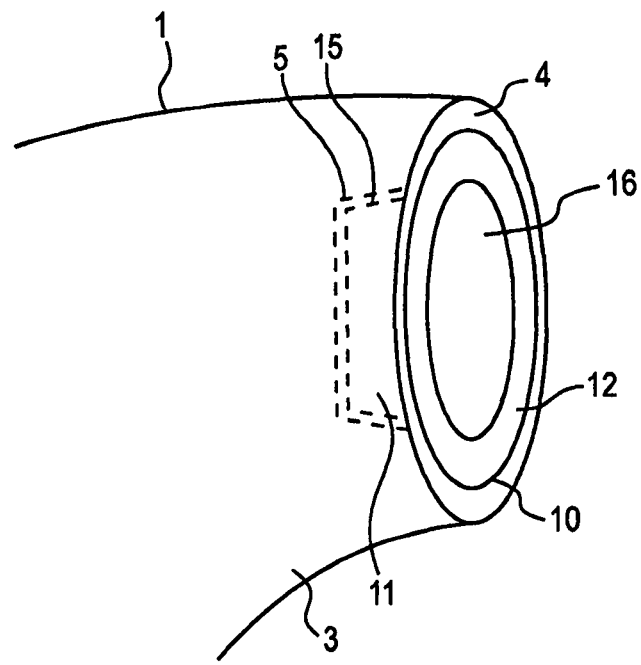
FIG. 10 is a perspective view of a bone fixation portion of the new implant disposed within a cavity in the glenoid.
Figure 11:
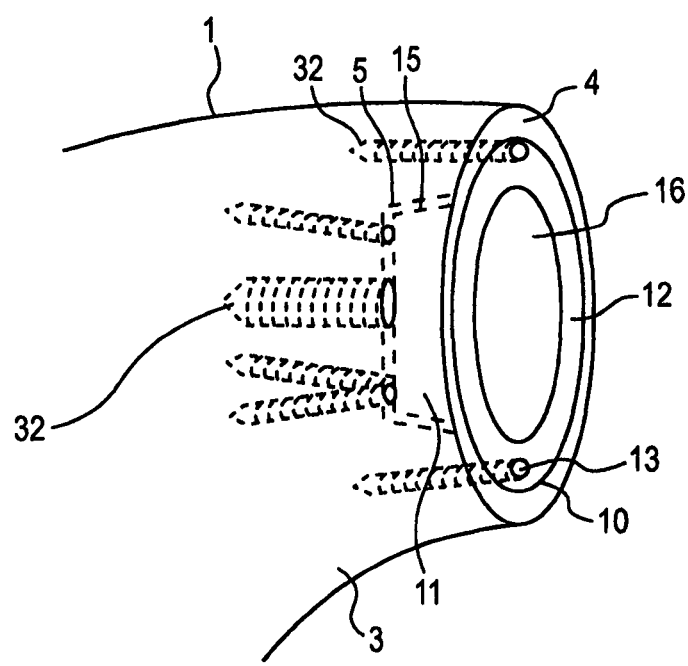
FIG. 11 is a perspective view of a screw fixation of a bone fixation portion of the new implant within a cavity in the glenoid.

The bone fixation portion 10 is positioned both in the prepared geometric glenoid cavity 5 in the glenoid vault bone 3 (inlay) and on the prepared glenoid bone surface 4 (onlay) (FIG. 3). The bone fixation portion 10 is a shallow complete or incomplete shell with a protruding element 11 which extends into the glenoid vault bone 3 (FIG. 10). The protruding element 11 is surrounded by a complete or incomplete peripheral rim 12 which rests upon the prepared perimeter of glenoid bone 4 surrounding the prepared glenoid cavity 5 (FIG. 10). The thickness of the peripheral rim may be minimalized to maximize the allowable thickness for the articulating portion 20 while still providing a sufficiently stable base. The protruding element 11 of the bone fixation portion 10 protrudes into the glenoid 1 to a specified depth such that it is sufficient for the bone fixation portion 10 to be securely seated within the glenoid 1 and for the articulating portion 20 to fit therein with the intermediate coupling portion 24 while preserving as much glenoid bone 3 as possible. The bone fixation portion 10 may have different embodiments with or without a peripheral rim 12 or with variable geometric dimensions with optional cannulations 13 (FIG. 11). The bone ingrowth surface 15 of the protruding element 11 of the bone fixation portion 10 of the glenoid implant 30 can possess a convex dome, cylinder, cone, triangle, square, trapezoid, double cylinders, other complex geometric shape, or other multiple protruding dimensions for engagement in the prepared glenoid cavity 5. For example, FIG. 4A shows an end view of an embodiment of a bone-fixation portion 10 having a square protruding portion 15A. The cannulations 13 can be arranged to place screws 32 to add fixation strength (FIG. 11). The cannulations 13 can be limited to the protruding element 11 of the bone fixation portion 10 rather than the peripheral rim 12 to allow the rim 12 to be of minimal thickness. Alternatively, cannulations 13 can exist in either the peripheral rim 12 or in the protruding element 11 or both. Screws 32 can compress the bone fixation portion 10 against the glenoid bone vault 5 and surface 4 and/or lock at a fixed angle and depth in the cannulations 13 of the bone fixation portion 10. The bone fixation portion 10 can be customized with variable peripheral rim 12 thickness and shape to fit an irregular or damaged glenoid surface 4A (FIGS. 8, 9).

Figure 5K:
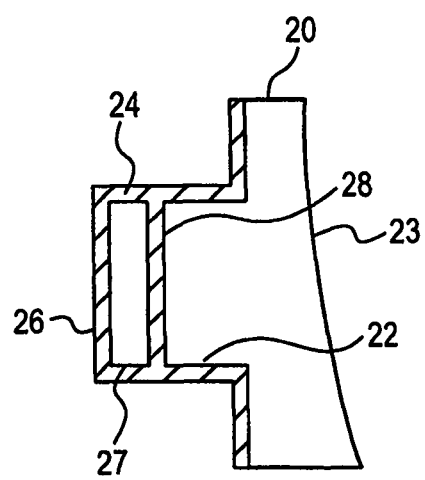
FIG. 5K is an enlarged cross-sectional view of the new implant's coupling portion with internal bridging reinforcements engaging a protruding element of the new implant's articulating portion.
Figure 5L:
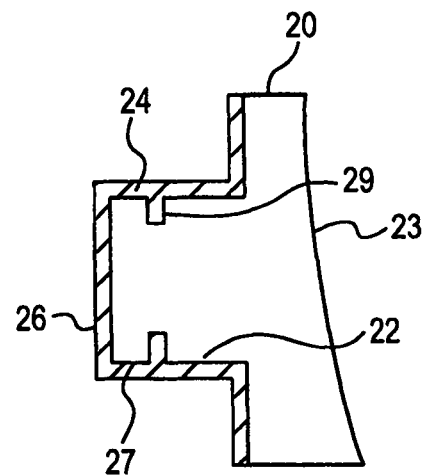
FIG. 5L is an enlarged cross-sectional view of the new implant's coupling portion with internal surface irregularities engaging a protruding element of the new implant's articulating portion.

The articulating surface portion 20 of the glenoid implant 30 has a smooth articulating surface 23 for contacting a humerus and uses the connecting surface 26 provided by the intermediate coupling portion 24 for disengageable connection to the connecting surface 16 of the bone fixation portion 10 (FIG. 4). The connecting surface 26 and intermediate coupling portion 24 may be of similar or different material than the articulating surface portion 20. Connecting surface 26 is also configured to substantially conform to the connecting surface 16 of the bone fixation portion 10, including its protruding element 11 and peripheral rim 12. However, the connecting surface 26 of the intermediate coupling portion 24 may be continuous or discontinuous in a variety of configurations allowing for complete or incomplete contact with the connecting surface 16 of the bone fixation portion 10, and also allowing for a variety of configurations dictated by connecting surface 22 on the non-articulating side of the articulating portion 20 (FIGS. 5A-5L). The intermediate coupling portion 24 may also possess internal bridging reinforcements 28 or irregularities 29 of its connecting surface 27 to improve the connection with the articular portion 20 (FIGS. 5K, 5L). The planar or concave articulating surface portion 20 can be of variable thickness to correct glenoid version, tilt or other deformity (FIGS. 5E, 5H, 5J).

Figure 15:
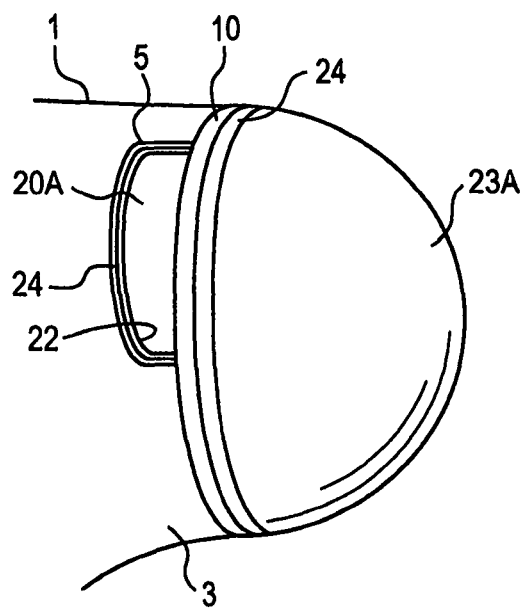
FIG. 15 is a perspective view of the new implant with a convex articulating surface portion arranged to extend over an entire glenoid surface and having a coupling engagement element fixed off-center from a central axis of the articulating surface portion.
Figure 16A:
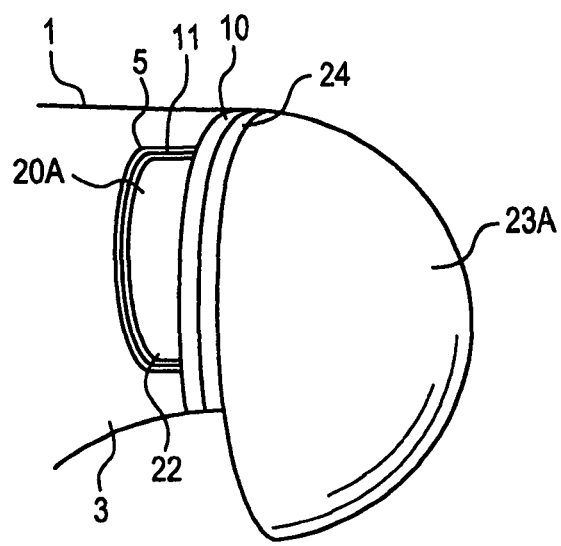
FIG. 16A is a perspective view of the new implant which has a convex articulating portion with an offset coupling element disposed in a cavity in the glenoid and part of the articulating surface portion extending outside the limits of the glenoid.
Figure 16B:
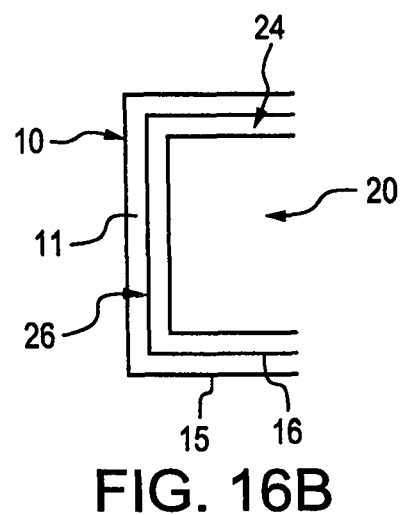
FIG. 16B is an enlarged sectional view of a segment of a protruding element on an articulating portion of the new implant shown in FIG. 16A assembled with a bone fixation portion of the implant inside the cavity in the glenoid.
Figure 17A:
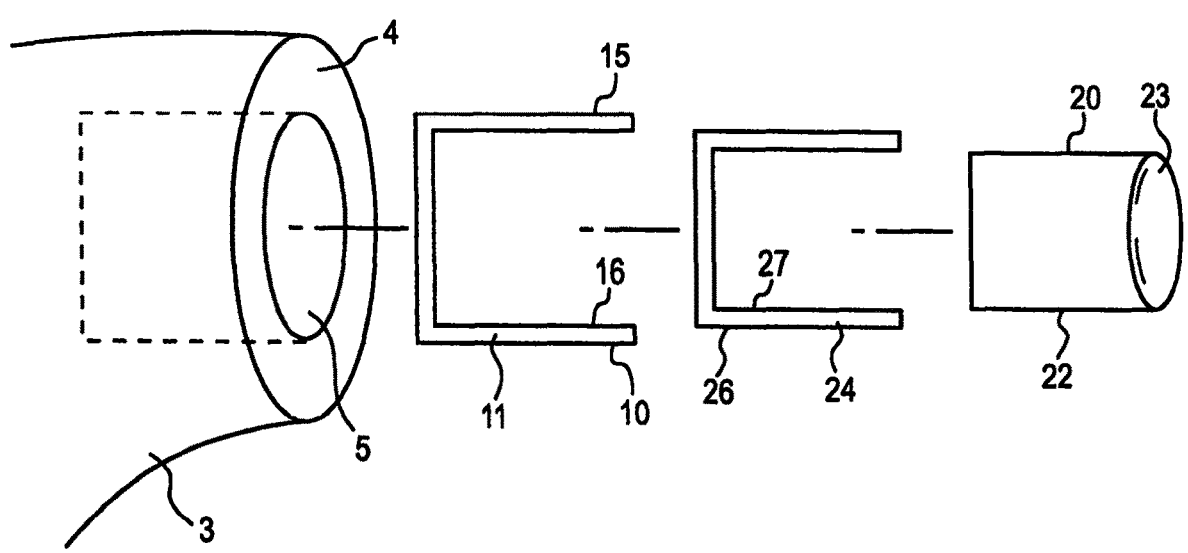
FIG. 17A is an exploded view an alternative form of the new glenoid implant which includes a rimless bone fixation portion, a coupling portion and a concave articulating surface portion.
Figure 17B:
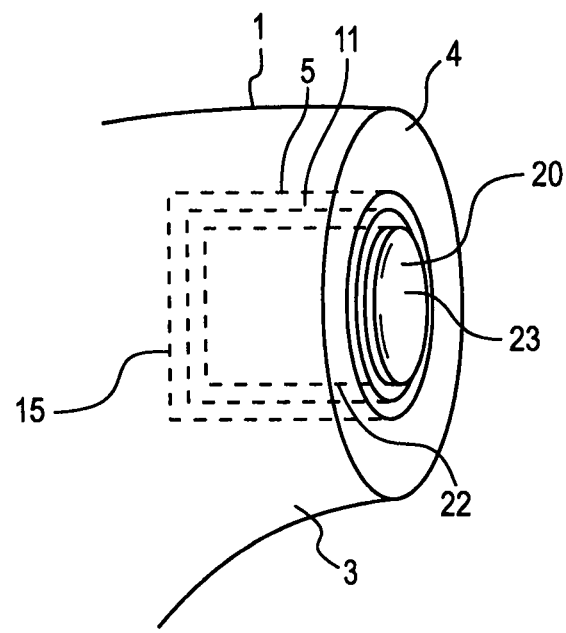
FIG. 17B is a perspective view of the new glenoid implant shown in FIG. 17A with a rimless bone fixation portion, a coupling and a concave articulating surface portion applied to a prepared surface in the glenoid.
Figure 17C:
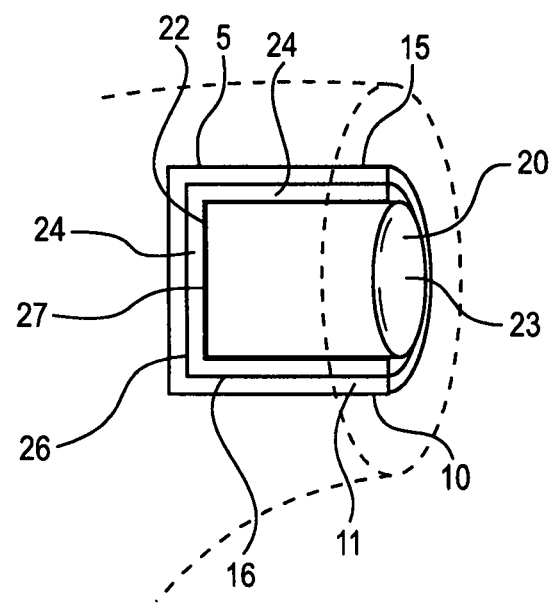
FIG. 17C is an enlarged sectional view of the new glenoid implant with a rimless bone fixation portion, a coupling portion and a concave articulating portion assembled together.
Figure 18A:
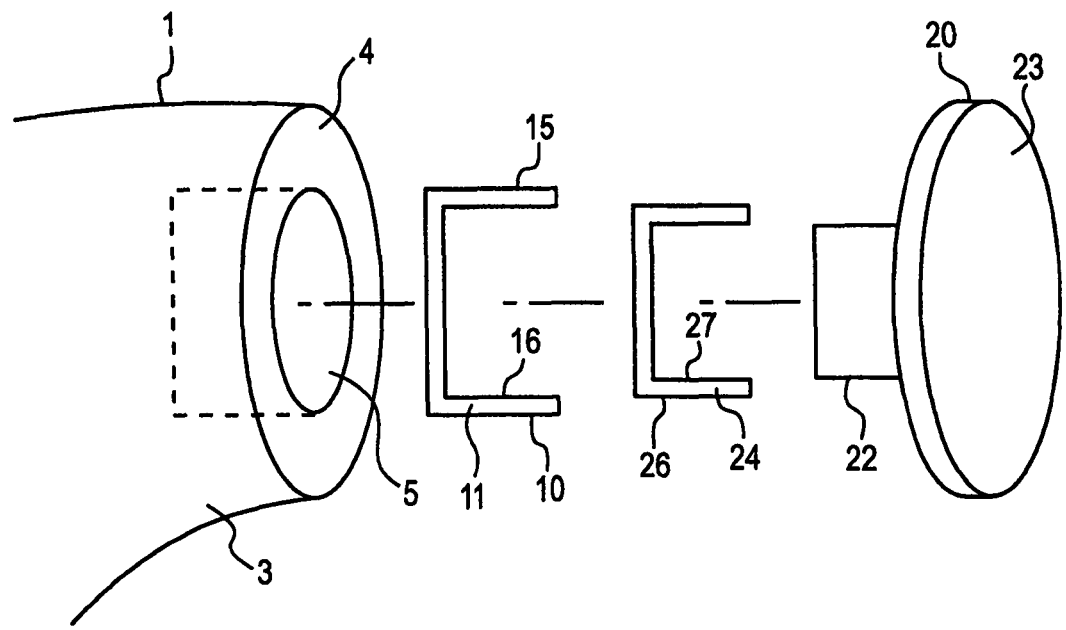
FIG. 18A is an exploded view of the new glenoid implant with a rimless bone fixation portion, a coupling portion and a full concave articulating portion.
Figure 18B:
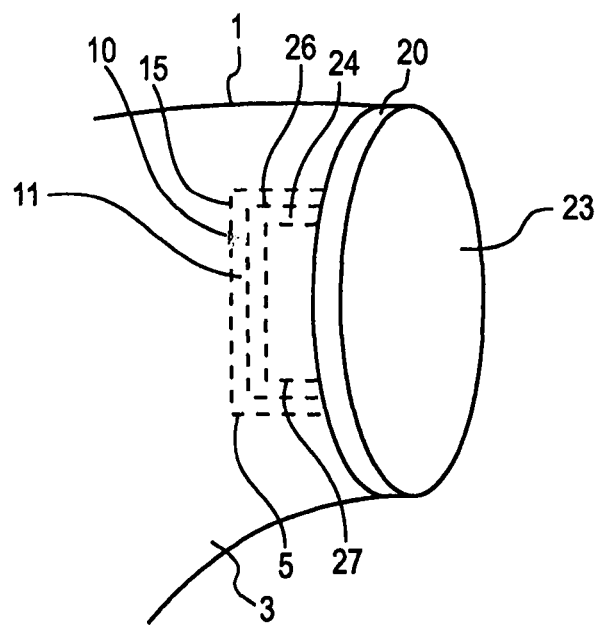
FIG. 18B is a perspective view of the new glenoid implant with a rimless bone fixation portion, a coupling portion and a full concave articulating portion applied to a prepared surface in the glenoid cavity.
Figure 19A:
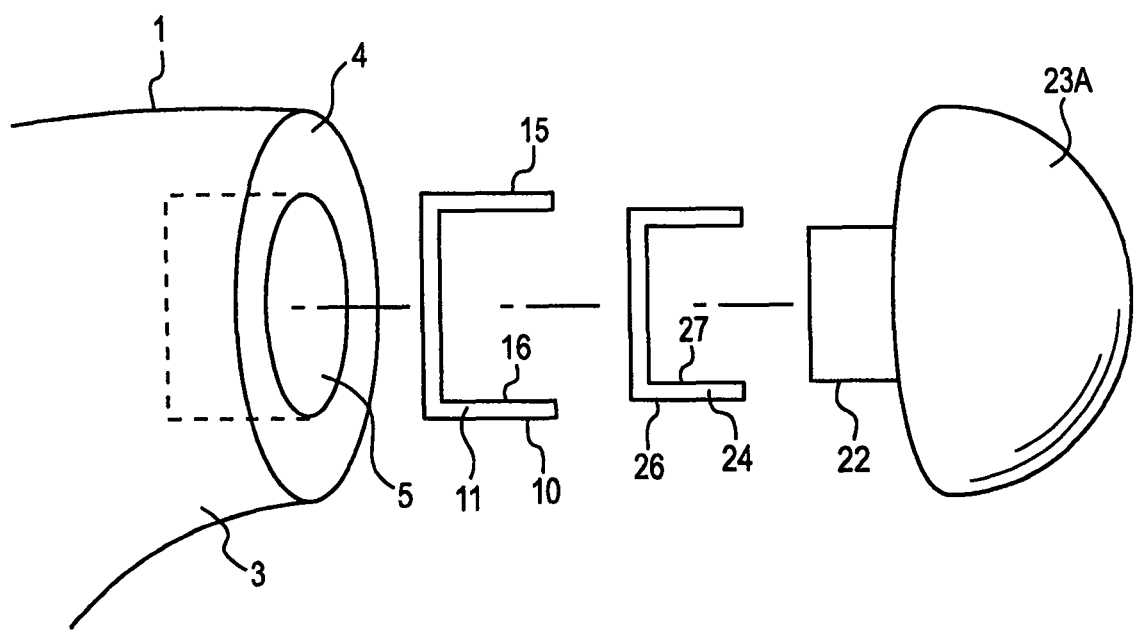
FIG. 19A is an exploded view of the new glenoid implant with a rimless bone fixation portion, a coupling portion and a convex articulating portion.
Figure 19B:
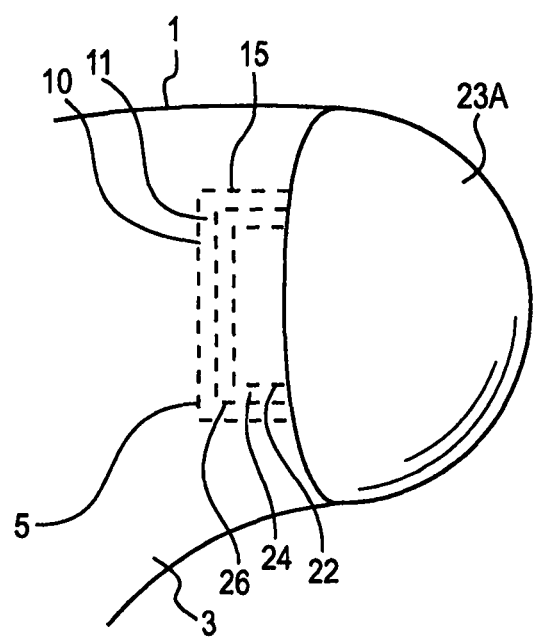
FIG. 19B is a perspective view of the new glenoid implant with a rimless bone fixation portion, a coupling portion and a convex articulating portion applied to a prepared surface in the glenoid cavity.

The protruding element 11 and its companion elements 24A and 20A may be offset from the centers of their respective portions, the bone fixation portion 10, the intermediate coupling portion 24, and/or the articulating portion 20 (FIGS. 7, 15, 16A). The bone fixation portion 10, intermediate coupling portion 24, and/or the articulating portion 20 may be rimless, without a peripheral rim (FIGS. 5A, 5B, 17A, 17B, 18A, 18B, 19A, 19B).

The glenoid surface 2 is prepared with a relatively planar reamer to mate with the peripheral onlay rim 12 of the bone fixation portion 10 of the glenoid implant 30. The central glenoid vault 3 is prepared by reaming, cutting and/or impacting it to create a geometric shaped cavity 5 within the glenoid 1. After inserting the protruding element 11 of bone fixation portion 10 into the glenoid cavity 5 and the peripheral rim 12 onto the prepared glenoid surface 4, screw(s) 32 can be inserted into optional cannulations 13 in the bone fixation portion 10 and the surrounding glenoid and scapular bone 1 to provide compressive and rigid locking fixation of the bone fixation portion 10 to the glenoid bone 1 (FIGS. 10, 11). The bone adherent and ingrowth surface 15 of the bone fixation portion 10 will provide a stable, long lasting connection. Any of the screws 32 can act as a stable fixed angle post to provide rigid positioning of the bone fixation portion 10.

Figure 12:
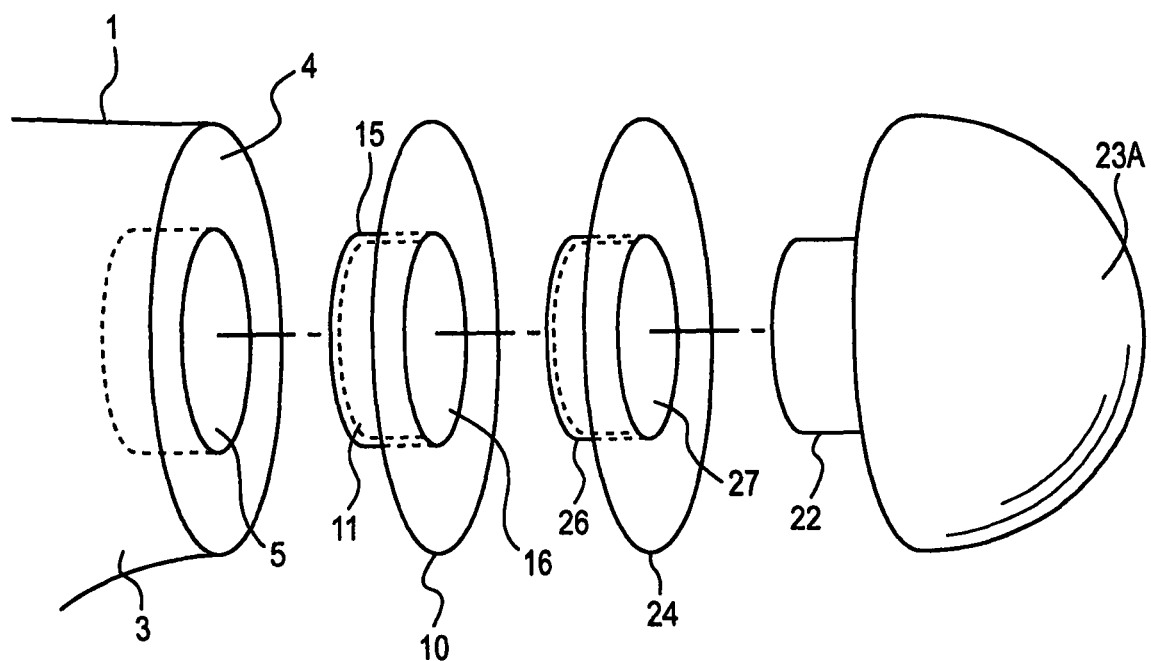
FIG. 12 is an exploded view of an alternative form of the new implant having a bone fixation portion, an intermediate coupling portion, and a convex articulating portion instead of a concave articulating portion.
Figure 13A:
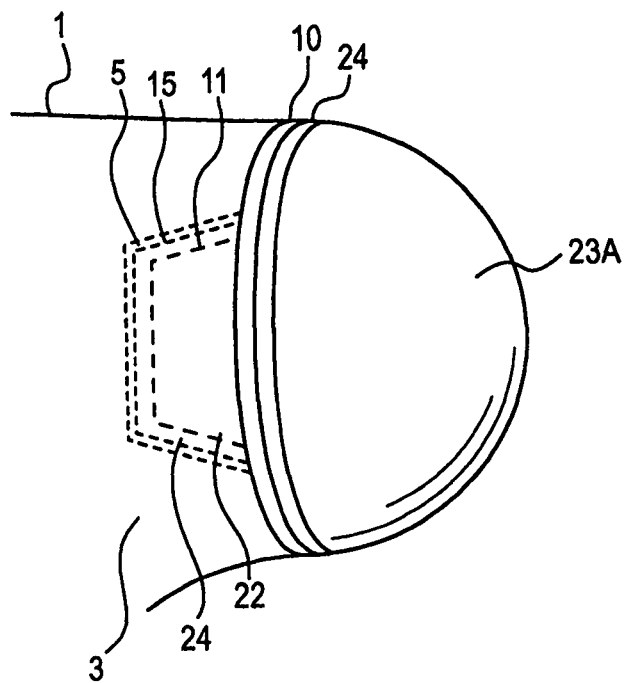
FIG. 13A is a perspective view of the new implant with the convex articulating portion, fully assembled and installed in a cavity in the glenoid.
Figure 13B:
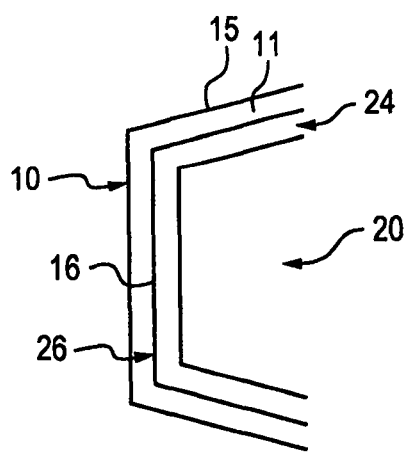
FIG. 13B is an enlarged sectional view of a segment of a protruding element on an articulating portion of the new implant shown in FIG. 13A assembled with a bone fixation portion of the implant inside the glenoid cavity.
Figure 14:
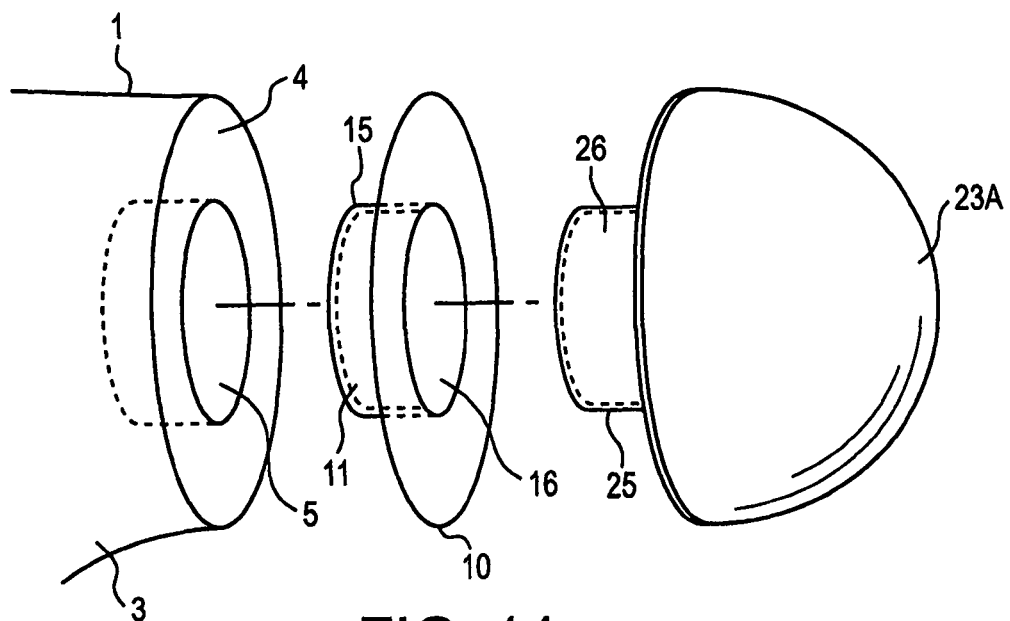
FIG. 14 is an exploded view of the new implant where the intermediate portion is constructed of similar material to that of the articular portion which makes up the non-articulating surface of the articular portion.

The articulating portion 20 of the novel glenoid implant 30 is then removably connected to the bone fixation portion 10 by means of the intermediate coupling portion 24 so as to allow later exchange of an articulating portion 20 having either a convex articulating surface 23A (FIGS. 12, 13A, 14) or a concave surface 23 (FIGS. 3, 4). In one embodiment of the present invention, the connecting surfaces 16 of the bone fixation portion 10 and 26 of the intermediate coupling portion 24 are of proper dimension and material to allow conical press fit connection of the articulating portion 20 to the bone fixation portion 10.

The articulating portion 20 of the novel glenoid implant 30 is then removably connected to the bone fixation portion 10 by means of the intermediate coupling portion 24 so as to allow later exchange of an articulating portion 20 having either a convex articulating surface 23A (FIGS. 12, 13A, 14) or a concave surface 23 (FIGS. 3, 4). In one embodiment of the present invention, for example, the connecting surfaces 16 of the bone fixation portion 10 and 26 of the intermediate coupling portion 24 are of proper dimension and material to allow a conical press fit connection of the portions 10 and 24. The press fit connection provides a durable but detachable connection between the articulating portion 20 and the bone fixation portion 10. Other interactive surfaces may be substituted for the press fit connection so long as such substitutions provide one or more similarly durable but detachable connections. The connecting surfaces 22 of the articulating portion 20 and 27 of the intermediate coupling portion 24 are of proper dimension and material to allow a durable interference fit connection of the portions 20 and 24. Additionally, the intermediate portion 24 may be of uniform material to the articular portion 20 and provide the connecting surface for the articulating portion 20 as this connection is not required to be detachable.

It is therefore intended that the foregoing detailed description be regarded as illustrative rather than limiting, and that it be understood that it is the following claims, including all equivalents, that are intended to define the spirit and scope of this invention.

I claim:

1. A glenoid implant comprising:
   a bone-fixation portion comprising a first side, a rim, an articular side, and a first protruding element on the first side, the bone-fixation portion defines a first recess open on the articular side, the rim extending from the first protruding element and surrounding the first protruding element, the first protruding element arranged to engage a bone surface inside a glenoid cavity, the first recess extends into the first protruding element;
   an articulating portion comprising a wear-resistant articulating surface arranged for sliding contact upon an articulating portion of a humerus, and a second protruding element opposite of the wear-resistant articulating surface; and
   a coupling portion between the bone-fixation and articulating portions, the coupling portion comprises a third protruding element on a first side of the coupling portion, the coupling portion defines a second recess on a second side of the coupling portion, the second recess extends into the third protruding element, the second protruding element is engaged with the coupling portion in the second recess and the third protruding element is engaged with the bone-fixation portion in the first recess to form a stable long-lasting but disengageable connection between the bone-fixation and articulating portions.

2. The implant of claim 1 in which the disengageable connection is a press fit connection.

3. The implant of claim 1 in which the first protruding element of the bone-fixation portion comprises a shape that is different from a shape of the first recess.

4. The implant of claim 1 in which the second protruding element is nested inside the third protruding element and the third protruding element is nested inside the first protruding element such that the first, second, and third protruding elements extend inside the glenoid cavity when implanted.

5. The implant of claim 1 in which the first protruding element of the bone-fixation portion is located off center from a center of the bone-fixation portion.

6. The implant of claim 1 in which a fastener is arranged to extend through a cannulation in the bone-fixation portion and maintain that portion in the glenoid cavity.

7. The implant of claim 6 in which the fastener is a screw.

8. The implant of claim 1 in which the bone-fixation portion includes bone ingrowth material on the outside of the first protruding element to promote bone growth and adhesion of the first protruding element to one or more walls of the glenoid cavity.

9. The implant of claim 1 in which the wear-resistant articulating surface of the articulating portion is planar.

10. The implant of claim 1 in which the wear-resistant articulating surface of the articulating portion is convex.

11. The implant of claim 1 in which the coupling portion comprises a rim, the rim extending from the third protruding element and surrounding the third protruding element.

12. The implant of claim 1 in which the coupling portion comprises a bridging reinforcement member extending between a plurality of wall portions bounding the second recess.

13. The implant of claim 1 in which the wear-resistant articulating surface of the articulating portion has a variable thickness dimension arranged to correct for glenoid bone abnormalities.

14. The implant of claim 1 in which the rim of the bone-fixation portion comprises a plurality of thicknesses arranged to correct for glenoid bone abnormalities.

15. The implant of claim 1 in which the wear-resistant articulating surface does not extend beyond a perimeter of the first protruding element of the bone-fixation portion.

16. The implant of claim 1 in which
   the first protruding element is a plurality of first protruding elements;
   the first recess is a plurality of first recesses;
   each of the plurality of first recesses extend into a respective protruding element of the plurality of first protruding elements;
   the second protruding element is a plurality of second protruding elements;
   the third protruding element is a plurality of third protruding elements;
   the second recess is a plurality of second recesses;
   each of the plurality of second recesses extend into a respective protruding element of the plurality of third protruding elements; and,
   the plurality of second protruding elements is engaged in the plurality of second recesses and the plurality of third protruding elements is engaged in the plurality of first recesses to form the stable long-lasting but disengageable connection between the bone-fixation and articulating portions.

17. The implant of claim 16 in which engagement of the plurality of third protruding elements in the plurality of first recesses restricts rotational movement of the articulating portion.

18. The implant of claim 1 in which the articulating portion comprises a wall opposite of the wear-resistant articulating surface, the second protruding element extends from the wall.

19. The implant of claim 1 in which the wear-resistant articulating surface of the articulating portion is concave.

20. The implant of claim 1 in which the second protruding element is disengageable from the coupling portion in the second recess and the third protruding element is disengageable from the bone-fixation portion in the first recess to allow a disengagement of the stable long-lasting but disengageable connection between the bone-fixation and articulating portions.

21. The implant of claim 1 in which the third protruding element is disengageable from the bone-fixation portion in the first recess to allow a disengagement of the stable long-lasting but disengageable connection between the bone-fixation and articulating portions.

22. A glenoid implant comprising:
a bone-fixation portion comprising a first side, an articular side, a rim, and a first protruding element on the first side, the first protruding element arranged to engage a bone surface inside a glenoid cavity, the bone-fixation portion defines a first hollow portion open on the articular side; and at least partially within the first protruding element, the rim extending from the first protruding element and surrounding the first protruding element;
an articulating portion comprising a wear-resistant articulating surface arranged for sliding contact upon an articulating portion of a humerus, and a second protruding element opposite of the wear-resistant articulating surface; and
a coupling portion between the bone-fixation and articulating portions, the coupling portion comprises a third protruding element on a first side of the coupling portion and a second opening on a second side of the coupling portion, the coupling portion defines a second hollow portion at least partially within the third protruding element and in communication with the second opening, the second protruding element is engaged with the coupling portion in the second hollow portion and the third protruding element is engaged with the bone-fixation portion in the first hollow portion to form a disengageable connection between the bone-fixation and articulating portions.

23. A glenoid implant of claim 22 in which the second protruding element is nested inside the third protruding element and the third protruding element is nested inside the first protruding element such that the first, second, and third protruding elements extend inside the glenoid cavity when implanted.

24. A glenoid implant comprising:
a bone-fixation portion comprising an articular side and a first connecting portion arranged to engage a bone surface inside a glenoid cavity, the bone-fixation portion defines a first recess open on the articular side, the entire bone-fixation portion arranged not to engage a bone surface outside the glenoid cavity;
an articulating portion comprising a wear-resistant articulating surface arranged for sliding contact upon an articulating portion of a humerus, and a second connecting portion opposite of the wear-resistant articulating surface; and
a coupling portion between the bone-fixation and articulating portions, the coupling portion comprises a third connecting portion, the first, second, and third connecting portions are configured to extend into the glenoid cavity, the second connecting portion is nested inside the third connecting portion and the third connecting portion is nested inside the first connecting portion and inside the first recess to form a stable long-lasting but disengageable connection between the bone-fixation and articulating portions; the bone-fixation portion is configured to shield the coupling portion from the glenoid cavity.

* * * * *